United States Patent
Margulies et al.

(10) Patent No.: US 12,390,551 B2
(45) Date of Patent: Aug. 19, 2025

(54) COMPOSITIONS USING IRON EXCIPIENTS AND THEIR USES INCLUDING FOR THE TREATMENT OF CANCER

(71) Applicant: Zetagen Therapeutics, Inc., Syracuse, NY (US)

(72) Inventors: Bryan S. Margulies, Liverpool, NY (US); Nikhil A. Thakur, Andover, MA (US)

(73) Assignee: Zetagen Therapeutics, Inc., Syracuse, NY (US)

( * ) Notice: Subject to any disclaimer, the term of this patent is extended or adjusted under 35 U.S.C. 154(b) by 0 days.

(21) Appl. No.: 18/462,292

(22) Filed: Sep. 6, 2023

(65) Prior Publication Data

US 2024/0016976 A1    Jan. 18, 2024

Related U.S. Application Data

(63) Continuation of application No. 17/143,468, filed on Jan. 7, 2021.

(60) Provisional application No. 63/053,277, filed on Jul. 17, 2020.

(51) Int. Cl.
| | |
|---|---|
| *A61L 27/12* | (2006.01) |
| *A61K 31/485* | (2006.01) |
| *A61L 27/04* | (2006.01) |
| *A61L 27/24* | (2006.01) |
| *A61L 27/54* | (2006.01) |

(52) U.S. Cl.
CPC ............ *A61L 27/12* (2013.01); *A61K 31/485* (2013.01); *A61L 27/042* (2013.01); *A61L 27/24* (2013.01); *A61L 27/54* (2013.01); *A61K 2300/00* (2013.01); *A61L 2300/204* (2013.01); *A61L 2300/602* (2013.01); *A61L 2300/802* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| | | |
|---|---|---|
| 4,678,470 A | 7/1987 | Nashef et al. |
| 5,281,265 A | 1/1994 | Liu |
| 5,882,944 A | 3/1999 | Sadee |
| 6,007,986 A | 12/1999 | Sadee |
| 6,270,979 B1 | 8/2001 | Sadee |
| 6,582,228 B2 | 6/2003 | Ricci et al. |
| 6,713,488 B2 | 3/2004 | Sadee et al. |

(Continued)

FOREIGN PATENT DOCUMENTS

| | | | |
|---|---|---|---|
| WO | WO-2004/050131 A1 | 6/2004 | |
| WO | WO-2009108934 A2 * | 9/2009 | ............. A61L 27/12 |

OTHER PUBLICATIONS

Thommen Medical (Ceros® TCP Granules and Putty Product Brochure, 2009, accessed online on Apr. 23, 2021 at <https://www.thommenmedical.com>. (Year: 2009).*

(Continued)

*Primary Examiner* — Carlos A Azpuru
*Assistant Examiner* — Casey S Hagopian
(74) *Attorney, Agent, or Firm* — Foley & Lardner LLP

(57) ABSTRACT

A bone graft composition comprising a calcium phosphate putty is provided. A method of repairing a bone defect in a patient by applying the bone graft composition is also provided.

13 Claims, 1 Drawing Sheet

Specification includes a Sequence Listing.

(56) References Cited

U.S. PATENT DOCUMENTS

| | | |
|---|---|---|
| 9,220,596 B2 | 12/2015 | Cook et al. |
| 2003/0055512 A1 | 3/2003 | Genin et al. |
| 2005/0251149 A1* | 11/2005 | Wenz ................... A61L 27/12 606/94 |
| 2007/0197573 A1 | 8/2007 | Sadee et al. |
| 2011/0144763 A1 | 6/2011 | Bagga et al. |
| 2012/0031305 A1* | 2/2012 | Shoji .................. A61L 27/46 106/656 |
| 2014/0213688 A1* | 7/2014 | Bezwada ............ A61L 24/046 523/116 |
| 2014/0341964 A1* | 11/2014 | McKay .............. A61L 24/0084 514/8.8 |
| 2015/0344882 A1* | 12/2015 | Thakur ................. A61P 19/08 514/282 |

OTHER PUBLICATIONS

Vlad et al. "Osteogenic biphasic calcium sulphate dihydrate/iron-modified α-tricalcium phosphate bone cement for spinal applications: In vivo study", Acta Biomaterialia 6 (Jul. 14, 2009) pp. 607-616. (Year: 2009).*

Oster et al. ("Natural history of skeletal-related events in patients with breast, lung, or prostate cancer and metastases to bone: a 15-year study in two large US health systems", Support Care Cancer, 21, pp. 3279-3286, 2013. (Year: 2013).*

Ju et al. ("Diagnosis and surgical management of breast cancer metastatic to the spine", World Journal of Clinical Oncology, 2014, vol. 5(3), pp. 263-271. (Year: 2014).*

"Iron (Fe) and water," Lenntech, accessed online Feb. 1, 2023 at https://www.lenntech.com/periodic/water/iron/iron-and-water.htm, 2023.

Jiang et al., "Mechanical Properties and Cytocompatibility Improvement of Vertebroplasty PMMA Bone Cements by Incorporating Mineralized Collagen," Materials, May 2015, 8:2616-2634.

Osteopal V Product Sheet, Heraeus, Revised Jun. 2020, accessed online at https://www.heraeus.com, 2020.

Thommen Medical (Ceros TCP Granules and Putty Product Brochure, 2009, accessed online on Apr. 23, 2021 at https://www.thommenmedical.com, 2009.

Vlad et al., "Osteogenic biphasic calcium sulphate dihydrate/iron-modified alpha-tricalcium phosphate bone cement for spinal applications: In vivo study," Acta Biomaterialia, Feb. 1, 2010 (online Jul. 14, 2009), 6(2):607-616.

* cited by examiner

FIG. 1A
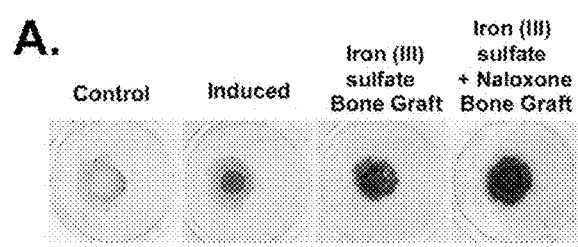
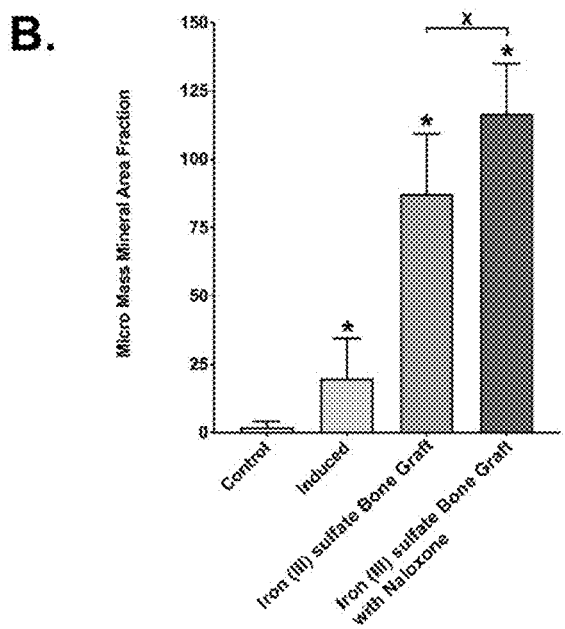
FIG. 1B

SEQUENCE LISTING

```
Sequence total quantity: 5
SEQ ID NO: 1           moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1
YGGFM                                                                     5

SEQ ID NO: 2           moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 2
YGGFL                                                                     5

SEQ ID NO: 3           moltype =    length =
SEQUENCE: 3
000

SEQ ID NO: 4           moltype = AA  length = 8
FEATURE                Location/Qualifiers
REGION                 1..8
                       note = Description of Artificial Sequence: Synthetic peptide
SITE                   1
                       note = MOD_RES - D-Phe
SITE                   4
                       note = MOD_RES - D-Trp
SITE                   7
                       note = MOD_RES - Pen - Penicillamine
source                 1..8
```

```
                    mol_type = protein
                    organism = synthetic construct
SEQUENCE: 4
FCYWKTXT                                                              8

SEQ ID NO: 5        moltype = AA  length = 50
FEATURE             Location/Qualifiers
REGION              1..50
                    note = Description of Artificial Sequence: Synthetic
                     polypeptide
source              1..50
                    mol_type = protein
                    organism = synthetic construct
SEQUENCE: 5
QSALDYFMFA VRCRHQRRQL VHFAWEHFRP RCKFVWGPQD KLRRFKPSSL                 50
```

COMPOSITIONS USING IRON EXCIPIENTS AND THEIR USES INCLUDING FOR THE TREATMENT OF CANCER

CROSS-REFERENCE TO RELATED APPLICATIONS

This application is a Continuation of U.S. application Ser. No. 17/143,468, filed Jan. 7, 2021, which claims priority to U.S. Provisional Application No. 63/053,277, filed on Jul. 17, 2020, the entire contents of which are incorporated herein by reference.

SEQUENCE LISTING

The instant application contains a Sequence Listing which has been submitted electronically in XML format and is hereby incorporated by reference in its entirety. Said XML copy, created on Sep. 6, 2023 is named 118922-0280_SL.xml and is 7,299 bytes in size.

BACKGROUND

Bone grafting is a surgical procedure performed to repair bone fractures that pose a significant health risk to the patient or fail to heal properly. Some kind of small or acute fractures can be cured but the risk is greater for large fractures like compound fractures. Bone generally has the ability to regenerate completely but requires a very small fracture space or some sort of scaffold to do so. Successful bone grafts result in osteoconduction, which refers to the ability of the bone graft material to passively permit bone growth, osteoinduction, wherein the bone graft encouraged undifferentiated cells to become active osteoblasts that form new bone tissue, and/or osteogenesis, which results in that living bone cells in the graft material contribute to bone remodeling. Osteogenesis only occurs with autograft tissue and allograft cellular bone matrices.

Bone grafts may be autologous, i.e. the bone graft material is harvested from the patient's own body, often from the iliac crest. Use of autogenous bone, however, subjects a patient to increased pain and discomfort, and an increased risk of infection, because it requires the patient to undergo additional surgery to recover the autogenous bone for use in the grafting procedure.

Bone grafts may be allograft, i.e., the bone graft material is derived from cadaveric bone, which is usually obtained from a bone bank. Allograft bone also subjects the patient to the risk of disease and graft rejection.

Bone graft material may be synthetic, and synthetic bone graft material is often made of hydroxyapatite or other naturally occurring and biocompatible substances with similar mechanical properties to bone. Most bone grafts are expected to be reabsorbed and replaced as the natural bone heals over a few months' time. However, synthetic bone graft material may have lower osteoconductive and/or osteoinductive properties than autograft and allograft material. Synthetic material may also subject the donor to microbial infections. There is therefore a great medical need for synthetic bone graft material with improved properties for healing bone injuries.

SUMMARY

In one aspect, a bone graft composition comprising a calcium phosphate putty and at least one of the following is provided: a hardening agent, an agent that controls the rate of curing, an acidifying agent, an iron excipient, collagen, and a diluent solution.

In some embodiments, the calcium phosphate putty comprises biphasic calcium phosphate particles. In some embodiments, the biphasic calcium phosphate particles comprise hydroxyapatite and tricalcium phosphate. In some embodiments, the biphasic calcium phosphate particles comprise about 20-60% hydroxyapatite and about 40-80% tricalcium phosphate. In some embodiments, the biphasic calcium phosphate particles have interconnected macro- and microporosity. In some embodiments, the biphasic calcium phosphate particles are in the shape of spherical particles, fibers, or irregular granules. In some embodiments, the calcium phosphate putty comprises biphasic calcium phosphate particles, wherein the biphasic calcium phosphate particles comprise hydroxyapatite and tricalcium phosphate, and wherein the bone graft composition further comprises collagen and naloxone.

In some embodiments, the bone graft composition further comprises a bioresorbable polymer.

In some embodiments, the bone graft composition has a density of 1-6 g/mL after mixing. In some embodiments, the force required to extrude the bone graft composition through a cannula, tube, or syringe is less than 80-N/m.

In some embodiments, the bone graft composition has no active agent. In some embodiments, the bone graft composition further comprises an active agent. In some embodiments, the bone graft composition is configured and arranged to deliver the active agent or other agent to a desired site in a patient.

In some embodiments, the bone graft composition comprises a network of reservoir and microchannels for storing and delivering the active agent. In some embodiments, the bone graft composition comprises a plurality of reservoirs, micro and/or nanotubules for storing and delivering the active agent. In some embodiments, the active agent is delivered at a controlled rate.

In some embodiments, the active agent is dissolved in a pharmaceutically suitable carrier. In some embodiments, the active agent dissolved in a pharmaceutically suitable carrier is sprayed or coated onto the synthetic bone graft.

In some embodiments, the active agent is an opioid growth factor receptor (OGFR) antagonist. In some embodiments, the OGFR antagonist is selected from the group consisting of naloxone, naltrexone, and a salt thereof. In some embodiments, the OGFR antagonist is administered with a diluent.

In some embodiments, the bone graft composition comprises the hardening agent, and wherein the hardening agent comprises sodium carbonate ($NaCO_3$) or iron sulfate ($FeSO_4$). In some embodiments, the bone graft composition comprises the hardening agent, and wherein the hardening agent comprises one or more compounds from the group consisting of calcium sulfate hemihydrate, calcium sulfate dihydrate, calcium sulfate anhydrite, monocalcium phosphate, dicalcium phosphate, tricalcium phosphate, tetracalcium phosphate, octacalcium phosphate, hydroxyapatite, calcium carbonate, magnesium carbonate, strontium carbonate, and sodium hydrogen phosphate.

In some embodiments, the ratio by weight of the hardening agent to compounds of the calcium phosphate salts is between 1:2 (hardening agents:calcium salts) and 3:4 (hardening agents:calcium salts).

In some embodiments, the bone graft composition comprises the acidifying agent, wherein the acidifying agent comprises one or more from the group of ascorbic acid, magnesium citrate, potassium citrate, sodium citrate, citric acid monohydrate, and acetic acid.

In some embodiments, the acidifying agent improves bioavailability of the active agent in the bone graft composition. In some embodiments, the acidifying agent promotes bone formation. In some embodiments, the acidifying agent increases tackiness of the bone graft material.

In some embodiments, the bone graft composition comprises a chromogenic agent. In some embodiments, the chromogenic agent comprises an activatable chromogenic agent. In some embodiments, the chromogenic agent colors the bone graft composition red, blue, orange, green, neon green, purple, brown, black, grey, or battleship grey.

In some embodiments, the bone graft composition comprises an antimicrobial agent. In some embodiments, the antimicrobial agent comprises one or more from the group of an antibiotic agent or an antifungal agent.

In some embodiments, the antibiotic agent comprises vancamycin, gentamicin, tobramycin, kanamycin, neomycin, ampicillin, methicillin, nafcillin, oxacillin, penicillin, ticarcillin, ciprofloxacin, vancomycin, cefazolin, cefepime, ceftiaxone, clindamycin, aztreonam, imipenem, quinupristin/dalfopristin, chloramphenicol, doxycycline, metronidazole, nitrofurantoin, polymycin B, tetracyclines, biomycin, chloromycetin, streptomycins, azactam, and any pharmaceutically acceptable salts thereof, and combinations thereof.

In some embodiments, the antifungal agent comprises one or more from the group of a polyene antifungal, an imidazole, a triazol, an allylamine, and an echinocandin. In some embodiments, the bone graft composition exhibits antimicrobial efficacy and/or antifungal efficacy. In some embodiments, the bone graft composition is not a dental resin.

In another aspect, a method of repairing a bone defect in a patient in need thereof is provided, the method comprising applying the bone graft composition disclosed herein to the bone defect.

In some embodiments, the bone defect is caused by a human disease or condition, and wherein the bone graft composition comprises an active agent for treating the human disease or condition. In some embodiments, the bone defect is caused by a human disease or condition, and wherein the bone graft composition does not contain an active agent for treating the human disease or condition. In some embodiments, the human disease or condition is one of several disorders of the spinal vertebral bones that requires surgical intervention to fuse the vertebral bones together. In some embodiments, the human disease or condition is one of several disorders of the appendicular bones, in which the appendicular bones require surgical intervention to fuse the bones together or repair a defect. In some embodiments, the human disease or condition is a bone void or defect that is not intrinsic to the stability of a bone structure, wherein the bone void or defect is created by surgery or traumatic injury, and wherein the bone graft composition fills the bone void or defect. In some embodiments, the bone defect comprises a void or gap of a bony skeletal system of the subject, wherein the void or gap is not intrinsic to the stability of the bony skeletal structure, and wherein the bone graft composition is packed into the void or gap.

In some embodiments, the surgical intervention comprises a lumbar interbody fusion (LIF) procedure. In some embodiments, the LIF procedure comprises anterior LIF, lateral LIF, transforaminal LIF, and posterior LIF. In some embodiments, the LIF procedure relieves associated pathologies, such as degenerative disc disease of a subject determined through radiography, by the creation of a bone defect via a surgical intervention. In some embodiments, the LIF procedure relieves associated neuromuscular deficits or physical deficits of a subject as determined by the Oswestry Disability Index (ODI) of the subject, by neurological evaluation of the subject, or by radiography of the subject.

In some embodiments, the human disease or condition is a cancer. In some embodiments the bone defect is caused by a cancer. Specific types of cancer include skin cancer (e.g. melanoma), connective tissue cancer (e.g. sarcoma, osteosarcoma, Ewing's sarcoma of bone, giant cell tumor), breast cancer, head and neck cancer, lung cancer (e.g. non-small cell lung carcinoma), gastric cancer, pancreatic cancer, ovarian cancer, cervical cancer, uterine cancer, anogenital cancer (e.g. testicular cancer), kidney cancer, bladder cancer, colon cancer, prostate cancer, central nervous system (CNS) cancer (e.g. neuroblastoma), retinal cancer, hematologic cancers, (e.g. multiple myeloma), and cancers of the lymphatic system (e.g., Hodgkin lymphoma and non-Hodgkin lymphoma), but are not limited to these.

In some embodiments, the bone defect is caused by a malignant tumor or the surgical removal of the malignant tumor via a resection procedure. In some embodiments, the malignant tumor comprises a breast cancer metastatic tumor. In some embodiments, the methods disclosed herein uses the disclosed bone graft compositions for reconstruction of the Metaphysis-Diaphysis of the humerus of the subject by using an Intercalary Allograft and Plate Fixation following malignant tumor resection such as a malignant breast cancer metastatic tumor.

In some embodiments, the bone graft composition is osteoconductive. In some embodiments, the bone graft composition is osteoinductive. In some embodiments, the bone graft composition is osteopromotive.

BRIEF DESCRIPTION OF THE DRAWINGS

FIGS. 1A-1B: MC3T3-E1 subclone 4 mouse calvaria derived osteoprogenitors cells were cultured as spheroids (micro masses) to become osteoblast bone cells. Cultures were either not treated (negative control), chemically treated to induce differentiation into osteoblasts (positive control), or cultured with the bone graft material containing the iron (III) sulfate excipient (Iron (III) sulfate bone graft). Cultures were grown for 7-days before either adding the bone graft material or chemical induction reagents. After an addition 12-days, cultures were stained with alizarin red stain (dark staining) for mineral deposition (FIG. 1A). The iron (III) sulfate cultures had significantly more staining than either control group. Cultures were then assessed for the quantity of mineral contained in the spheroids to determine if the mineral increased (FIG. 1B). The iron (III) sulfate bone graft cultures had significantly more mineral in the spheroids (*=$p<0.0001$) versus the negative control cultures. The mineral in the positive control cultures were not significantly different from the negative control cultures (ns=not significant).

DETAILED DESCRIPTION

Compositions, materials, methods, and kits for bone grafting and repairing and/or filling a void or gap in a bone are described herein. The present disclosure provides bone graft compositions with improved material properties and improved bioavailability of agents contained in the material. The present disclosure also provides bone graft compositions that include chromogenic agents that allow easy and convenient detection of the grafted material. In addition, bone graft compositions with improved anti-microbial features are included herein. Finally, the present disclosure provides bone graft compositions containing an active agent with therapeutic properties for treating diseases and conditions in which it is desirable or necessary to promote bone growth either by stimulating bone formation or preventing bone destruction.

I. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, the term "bone graft composition" means any malleable composition suitable for repairing bone defects. The bone graft composition may be a "calcium phosphate putty." In some embodiments, the calcium phosphate putty is a bone void filler.

As used herein, the term "active agent" means any, including chemical or biologic, that has been approved by a regulatory agency such as USFDA for the treaent of a specific indication.

The term "does not include an active agent" in the context of a composition or formulation means a composition or formulation that does not include any active agent as defined herein.

As used herein, the term "biocompatible" refers to the ability (e.g., of a composition or material) to perform with an appropriate host response in a specific application, or at least to perform without having a toxic or otherwise deleterious effect on a biological system of the host, locally or systemically.

As used herein, the term "osteoconductive" refers to the ability (e.g., of a composition or material) to passively permit bone growth (e.g., onto and/or into the material). As such, osteoconduction can be characterized as a passive process. Osteoconductive materials or compositions will only contribute to new bone growth in an area where there is already vital bone.

A material (e.g., a graft or implant) can be osteoconductive, for example, because it is configured to passively permit growth of bone on a surface of the material. In another example, a material can be osteoconductive, because it is configured to passively permit growth of bone into an opening (e.g., a pore) of the material.

As used herein, the term "osteoinductive" refers to the capability (e.g., of a composition or material) to actively stimulate a biological response which induces bone formation. As such, osteoinduction can be characterized as an active process. Osteoinductive materials or compositions induce de novo bone growth and can contribute to new bone growth in an area where there is no vital bone.

Osteoinduction can include the formation and/or stimulation of osteoprogenitor cells, such as osteoprogenitor cells in bodily tissue surrounding or proximate to a graft or implant.

As used herein, the term "osteopromotive" refers to the ability (e.g., of a composition or material) to promote de novo formation of bone by enhancing the osteoinductivity of osteoinductive materials. Osteopromotive compositions or materials enhance osteoinduction but are not inherently osteoinductive.

As used herein, the term "bioactive" refers to the capability (e.g., of a composition or material) to form a hydroxyapatite (HA) surface layer when immersed in simulated body fluid (SBF).

As used herein, the term "osteostimulative" refers to the capability (e.g., of a composition, material, or extract thereof) to enhance or actively stimulate proliferation of osteoblasts and differentiation of mesenchymal stem cells.

As used herein, the term "anti-bacterial" or "anti-microbial" refers to the capability (e.g., of a composition, material, or extract thereof) to inhibit the growth of microorganisms based on methods described in USP <51>.

As used herein, the term "biodegradable" refers to the capability of a material to be degraded, disassembled, and/or digested over time by action of a biological environment (including the action of living organisms, e.g., the patient's body) and/or in response to a change in physiological pH or temperature. Biodegradable, in the context of a human body environment, implies that the material is degraded, disassembled, and/or digested under normal physiological conditions.

As used herein, the terms "resorbable" and "bioresorbable" refers to the capability of a material to be broken down over a period of time and assimilated into the biological environment. Resorbable and bioresorbable, in the context of a human body environment, implies that the material is broken down over a period of time and assimilated into the body under normal physiological conditions.

As used herein, the term "moldable" refers to the property of being pliable, able to be compressed, shaped, and manipulated by force of hand, while maintaining integrity, homogeneity of the composition, physical properties, and performance properties.

As used herein, references to a weight of components of a bone graft composition or material described herein, such as the phrase "by weight," refer to the weight of the applicable component prior to being added to or mixed with another different component of the bone graft composition. For example, the weight can refer to an initial weight of the component measured out before further processing of the component into the bone graft composition.

As used herein, the phrase "non-load bearing application" refers to an application for repair of a void or gap in a bone or another bony structure in which the void or gap to be repaired is not intrinsic to the stability of the bone or bony structure.

As used here, the term "antagonist" is used interchangeably with "inhibitor" and refers to a substrate that blocks or suppresses the activity, function, effect, or expression of a target. In some embodiments, the target is a compound, a protein, a gene, a cell, or an agent. As used herein, the term "expression" refers to the amount a living cell produces of a target. In some embodiments, the inhibitor suppresses expression of a target gene or protein. In some embodiments, the inhibitor includes a compound that prevents binding of another molecule to an enzyme or molecular pump. In some embodiments, the inhibitor is a compound that causes down-regulation of the enzyme. In some embodiments, the inhibitor can be a competing or non-competing inhibitor.

The term "administering" as used herein includes prescribing for administration as well as actually administering and includes physically administering by the subject being treated or by another.

As used herein "subject," "patient," or "individual" refers to any subject, patient, or individual, and the terms are used interchangeably herein. In this regard, the terms "subject," "patient," and "individual" includes mammals, and, in particular humans, dogs, and cats. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The term "treating" or "treatment" covers the treatment of a condition causing or associated with a bone defect. For example, a cancer. Such treatment, in a subject, such as a human or veterinary patient, includes (i) inhibiting a cancer, i.e., arresting its development; (ii) relieving a cancer or disorder, i.e., causing regression of the cancer; (iii) slowing progression of the cancer; and/or (iv) inhibiting, relieving, or slowing progression of one or more symptoms of the cancer. For example, treatment of a cancer includes, but is not limited to, elimination of the cancer or the condition caused by the cancer, remission of the tumor, inhibition of the cancer, or reduction or elimination of at least one symptom of the tumor. Other examples of conditions causing or associated with a bone defect include, for example, diabetes mellitus, osteoporosis, lupus, rheumatoid arthritis, hyperthyroidism, celiac disease, asthma, and multiple sclerosis. Active agents for treating any of the above conditions are well known to the skilled artisan and fall within the scope of this disclosure.

The term "treating" or "treatment" can also cover the treatment via surgical intervention of a condition causing or associated with a bone defect due to biomechanical instability of the skeleton, degenerative conditions associated with ageing, or due to trauma. Patients can be human or veterinary patients. For example, spine fusion due to degenerative disc disease. Such treatment, in a subject, such as a human, includes removing the degenerative intervertebral disc, placing an intervertebral spacer or 'cage' between the two vertebral segments in a treatment segment, placing the bone graft material into the spacer/cage, and then metal rods and screws to mechanically stabilize the spine. After several months the bone of the vertebral segments fuses resulting in a mechanically stable vertebral segment. Other conditions include fracture, osteotomy, arthroplasty, reconstructive procedures, oral augmentation (i.e., any dental repairs including ridge augmentation, sinus lift, or socket repair), and defect (e.g., void filler) repair. In some embodiments, the bone defect comprises a void or gap of a bony skeletal system of the subject, wherein the void or gap is not intrinsic to the stability of the bony skeletal structure. The void or gap in the bony skeletal system of the subject may be treated by packing the bone graft composition gently into the void or gap.

The condition may also be disorders of the appendicular bones, in which the appendicular bones require surgical intervention to fuse the bones together or repair a defect. In some embodiments, the human disease or condition is a bone void or defect that is not intrinsic to the stability of a bone structure, wherein the bone void or defect is created by surgery or traumatic injury, and wherein the bone graft composition fills the bone void or defect. In some embodiments, the human disease or condition is a bone void or defect that is not intrinsic to the stability of a bone structure, wherein the bone void or defect is created by surgery or traumatic injury. In some embodiments, the surgical intervention comprises lumbar interbody fusion (LIF) procedure. In some embodiments, the LIF procedure comprises anterior LIF, lateral LIF, transforaminal LIF, and posterior LIF. In some embodiments, the LIF procedure relieves associated pathologies, such as degenerative disc disease of a subject determined through radiography, by the creation of a bone defect via a surgical intervention. In some embodiments, the LIF procedure relieves associated neuromuscular deficits or physical deficits of a subject as determined by the Oswestry Disability Index (ODI) of the subject, by neurological evaluation of the subject, or by radiography of the subject.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar beginning compound by attaching another molecule or atom to the beginning compound. Further, derivatives, according to the invention, encompass one or more compounds formed from a precursor compound through addition of one or more atoms or molecules or through combining two or more precursor compounds.

II. Calcium Phosphate Bone Graft Composition

A bone graft composition, or material, according to an embodiment facilitates repair or regeneration of bone at a target repair site. For example, in some embodiments, the bone graft composition can be osteoconductive, osteoinductive, bioactive, osteostimulative, antibacterial or any combination thereof. The target repair site can be, for example, a void, gap, or other defect in a bone or other bony structure in a body of a patient. For example, as described in more detail below, the bone graft composition facilitates bone growth at a target repair site in the spine, pelvis, an extremity, the cranium, or another bone or bony structure in the patient's body. The bone graft composition can be implanted, extruded, molded, or otherwise placed at the target repair site. For example, in some embodiments, the bone graft composition can be implanted, extruded, molded, or placed at the target repair site in a non-load bearing application. In other embodiments, the bone graft composition can be implanted, extruded, molded, or placed at the target repair site with appropriate orthopedic 'hardware' (i.e. screws, plates, rods, cages/spacers, prosthetics, hip implants, knee implants, acetabular implants, etc.) in load bearing applications.

In some embodiments, the bone graft composition is a calcium phosphate composition.

In some embodiments, the calcium phosphate is chosen from the following: hydroxyapatite ($Ca_5(OH)(PO_4)_3$), beta-tricalcium phosphate (beta-$Ca_3(PO_4)_2$), calcium phosphate dibasic ($CaHPO_4$), or calcium phosphate tribasic ($Ca_5(OH)(PO_4)_3$), monocalcium phosphate monohydrate ($Ca(H_2PO_4)_2 \cdot H_2O$), dicalcium phosphate dihydrate ($CaHPO_4 \cdot 2H_2O$), octocalcium phosphate ($Ca_8H_2(PO_4)_6 \cdot H_5H_2O$), monocalcium phosphate ($Ca(H_2PO_4)_2$), alpha-tricalcium phosphate (alpha-$Ca_3(PO_4)_2$), sintered hydroxyapatite ($Ca_{10}(PO_4)_6(OH)_2$), oxyapatite ($Ca_{10}(PO_4)_6O$), or tetracalcium phosphate ($Ca_4(PO_4)_2O$).

In some embodiments, the hydroxyapatite is a precipitated hydroxyapatite material with the chemical formula $Ca_{10-x}(HPO_4)_x(PO_4)_{6-x}(OH)_{2-x}$, in which 'x' may vary between 0 and 2.

In some embodiments, the tricalcium phosphate is a precipitated amorphous calcium phosphate with the chemical formula $Ca_3(PO_4)_2 \cdot nH_2O$, in which 'n'=3-4.5 and the H2O content is 15%-20%.

In some embodiments, the size of individual grains (or particles) of the hydroxyapatite material ranges from 1-nm to 5-mm.

In some preferred embodiments, the grain size for the hydroxyapatite will be selected from the following sizes: 10-micron, 75-micron, 86.4-micron, 125-micron, 147-micron, 212-micron, 368-micron, or 740-micron. In these embodiments, the grain size will be understood to represent the max size and that a range will exist with potentially smaller particles of the material.

In some embodiments, the size of individual grains (or particles) of the beta-tricalcium phosphate material ranges from 1-nm to 5-mm.

In some preferred embodiments, the grain size of the beta-tricalcium phosphate will be selected from the following sizes: 100-micron, 125-micron, 212-micron, 304-micron, 645-micron, 500-micron, or 1000-micron. In these embodiments, the grain size will be understood to represent the max size and that a range will exist with potentially smaller particles of the material.

In some embodiments, the tricalcium phosphate will be a mixture of beta-tricalcium phosphate and alpha-tricalcium phosphate.

In some embodiments, the calcium phosphate salts could be anhydrous, monohydrate, dihydrate, or any $xH_2O$ hydrate isoform.

In a preferred embodiment, the calcium phosphate salts contained in the preferred formulation of the bone graft material are sintered hydroxyapatite ($Ca_{10}(PO_4)_6(OH)_2$), beta-tricalcium phosphate (beta-$Ca_3(PO_4)_2$), calcium phosphate dibasic ($CaHPO_4$), and calcium phosphate tribasic ($Ca_5(OH)(PO_4)_3$).

III. Hardening Agents

In some embodiments, the bone graft composition comprises a hardening agent. A hardening agent improves the degree of hardening of the bone graft composition.

In some embodiments, the hardening agent may be sodium carbonate ($Na_2CO_3$).

In some embodiments, the hardening agent may also be calcium sulfate anhydrate ($CaSO_4$), calcium sulfate hemihydrate ($CaSO_4 \cdot 0.5H_2O$), calcium sulfate dihydrate ($CaSO_4 \cdot 2H_2O$), calcium carbonate ($CaCO_3$), magnesium carbonate ($MgCO_3$), strontium carbonate ($SrCO_3$), and bioglass.

In some embodiments, the hardening agent salts could be anhydrous, monohydrate, dihydrate, or any $xH_2O$ hydrate isoform.

In a preferred embodiment, the hardening agent contained in the preferred formulation of the bone graft material is sodium carbonate ($Na_2CO_3$).

IV. Agents that Control the Rate of Curing

In some embodiments, the bone graft composition comprises a curing agent. A curing agent improves the rate of curing of the bone graft composition.

In some embodiments, the curing agent may comprise calcium oxide (CaO), magnesium oxide (MgO), sodium phosphate dibasic ($Na_2HPO_4$), sodium pyrophosphate tetrabasic ($Na_4P_2O_7$), sodium orthophosphate ($Na_3PO_4$), or sodium phosphate monobasic ($NaH_2PO_4$).

In some embodiments, the sodium phosphate salts may comprise anhydrous, monohydrate, dihydrate, or any $xH_2O$ hydrate isoform.

In a preferred embodiment, the agents that control the rate of curing comprise calcium oxide (CaO), magnesium oxide (MgO), and sodium phosphate dibasic ($Na_2HPO_4$).

V. Acidifying Agents

It is a discovery of the present inventors that adding acidifying agents to a bone graft composition provides improved material properties, dissolution, bioavailability of small molecules, promotes bone formation, and improves handling properties. An acidifying agent is defined as a chemical agent, molecule, or ion capable of donating a proton (hydrogen ion H+; known as a Brønsted-Lowry acids); or, alternatively, capable of forming a covalent bond with an electron pair (known as a Lewis acid).

In some embodiments, the bone graft composition comprises the acidifying agent, wherein the acidifying agent comprises L-ascorbic acid ($C_6H_8O_6$), ascorbate 2-phosphate sesquimagnesium salt hydrate ($C_{12}H_{12}O_{10}(PO_4)_2Mg_3 \cdot xH_2O$), sodium citrate dihydrate ($Na_3C_6H_5O_7 \cdot 2H_2O$), magnesium citrate($MgC_6H_6O_7$), potassium citrate monohydrate ($K_3C_6H_5O_7 \cdot H_2O$), citric acid monohydrate ($C_6H_8O_7 \cdot H_2O$), and acetic acid ($C_2H_4O_2$).

In some embodiments, the acidifying agent could be anhydrous, monohydrate, dihydrate, or any $xH_2O$ hydrate isoform.

In some embodiments, the acidifying agent is a component of the bone graft material and is a salt or ester chemical species that produces a polyatomic anion that forms in a solution and when in solution otherwise conforms to the conventions that define a chemical species as an acid.

In a preferred embodiment, the acidifying agent comprises one or more of L-ascorbic acid ($C_6H_8O_6$), citric acid monohydrate ($C_6H_8O_7 \cdot H_2O$), and acetic acid ($C_2H_4O_2$).

VI. Iron Excipients

It is a discovery of the present inventors that adding iron excipients, in the form of iron salts, iron oxides, iron compounds, iron alloys, and elemental iron to the bone graft composition enables the following: 1) As a chromogenic agent, iron excipients provide for easy detection of where the putty is relative to the adjacent bone. In addition, iron excipients as chromogenic agents allow visualization of adequate mixing based on evaluating the uniformity of color upon mixing the liquid and solid precursors of the bone graft composition. 2) Iron excipients modulate the material properties of the bone graft material by functioning as agents that control the rate of curing and also as agents that contribute to hardening. 3) Iron excipients act as contrast agents during x-radiographic imaging (X-radiographs and computed tomography). 4) Iron excipients contribute to osteogenesis.

In some embodiments, chromogenic agents comprise a chromogen that is also an iron excipient. As used herein, the term "chromogen" is any chemical species that is an iron excipient that also changes color upon dissolving in a solvent.

In some embodiments, chromogenic agents comprise an activateable chromogenic agent.

In some embodiments, the chromogenic agent colors the bone graft composition red, orange, brown, black, or grey. In some preferred embodiments, the chromogenic agent colors the bone graft composition orange, red, brown, or grey.

In some embodiments, the iron excipient is iron (III) sulfate hydrate ($Fe_2(SO_4)_3$), iron (III) chloride ($FeCl_3$), iron (III) citrate ($FeC_6H_5O_7$), iron (III) oxide ($Fe_2O_3$), iron (III) hydroxide oxide ($Fe(OH)O$), iron (III) phosphate ($FePO_4$), ammonium iron (III) citrate ($C_6H_8O_7 \cdot xFe_3 + \cdot yNH_3$), elemental iron particles (Fe), iron (III) fluoride ($FeF_3$), iron (II) sulfate heptahydrate ($FeSO_4 \cdot 7H_2O$), iron (II) ammonium sulfate hexahydrate ($Fe(NH_4)_2(SO_4)_2 \cdot 6H_2O$), iron (II) chloride ($FeCl_{12}$), iron (II) disulfide ($FeS_2$), iron(II) sulfate heptahydrate ($FeSO_4 \cdot 7H_2O$), and iron (II) lactate hydrate ($Fe(CH_3CH(OH)COO)_2 \cdot xH_2O$), iron (II) L-ascorbate ($FeC_{12}H_{14}O_{12}$), and iron (II) fluoride ($FeF_2$).

In a preferred embodiment, the iron excipient is iron (III) sulfate hydrate ($Fe_2(SO_4)_3$).

VII. Collagen

It is a discovery of the present inventors that collagen powders and liquid collagen preparations can be used to create a bone graft material. Type-I collagen is a white, hygroscopic material commonly used as a component of bone grafts.

Collagen powders are preparations of a collagen material in which the collagen polymer is cleaved chemically or enzymatically or through any conventional means that produces fragments of collagen of a particular size or range of sizes. In this preparation, the collagen could be 1-nm to 100-micron produced through reverse dialysis. In another preparation, the collagen could be cleaved enzymatically to produce fragments between 100-micron to 300-micron. In yet another preparation, the collagen could be ground or milled mechanically and then passed through a filter to produce fragments between 200-micron to 5-mm. In another embodiment, the collagen has a particle size of from 25-microns to 750-microns. In another embodiment, the collagen has a particle size of from 1-micron to 1.5-mm. In still yet another preparation, collagen is ground or milled at low temperatures (cryogrinding) to produce fragments from 1-micron to 5-mm.

A liquid collagen is a preparation of collagen that contains the soluble fraction of collagen that is dissolved in a solution. In this preparation, the collagen is soaked in an acid solution, and/or it is heated between 100-degrees Celsius and 300-degrees Celsius, and/or it is heated in a pressurized environment, and/or it is filtered to produce a fragment of a particular size. In yet another preparation, the liquid collagen is produced through grinding or milling collagen suspended in a solution using rotor stator to produce collagen fragments between 1-micron to 1-mm.

In a preferred preparation, the collagen is milled to produce powder with one of the following sized fragments: 10-micron, 15-micron, 20-micron, 25-micron, 30-micron, 35-micron, 50-micron, 55-micron, 60-micron, 65-micron, 70-micron, 75-micron, 80-micron, 85-micron, 90-micron, 95-micron, 100-micron, 150-micron, 200-micron, 250-micron, 300-micron, 350-micron, 400-micron, 450-micron, 500-micron, 750-micron, or 1000-micron fragment. In another preparation, the collagen powder is composed of a range of fragment sizes from the above.

VIII. Antimicrobial Agents

As used herein, the term "antimicrobial agent" refers to agent that kills microorganisms or stops their growth. Antibiotics are antimicrobial agents that kill bacteria, and antifungal agents are agents that kill fungi.

Accordingly, in some embodiments, the bone graft composition comprises an antimicrobial agent. In some embodiments, the antimicrobial agent comprises an antibiotic agent, or an antifungal agent.

In some embodiments, the antibiotic agent comprises vancamycin, gentamicin, tobramycin, kanamycin, neomycin, ampicillin, methicillin, nafcillin, oxacillin, penicillin, ticarcillin, ciprofloxacin, vancomycin, cefazolin, cefepime, ceftriaxone, clindamycin, aztreonam, imipenem, quinupristin/dalfopristin, chloramphenicol, doxycycline, metronidazole, nitrofurantoin, polymycin B, tetracyclines, biomycin, chloromycetin, streptomycins, azactam, any pharmaceutically acceptable salts thereof and combinations thereof.

In some embodiment, the antifungal agent comprises a polyene antifungal, an imidazole, a triazol, an allylamine, or an echinocandin. In some embodiments, the polyene antifungal comprises amphotericin B, candicidin, filipin, hamycin, natamycin, nystatin, rimocidin, imidazole, triazole, and thiazole. In some embodiments, the imidazole comprises bifonazole, butoconazole, clotrimazole, econazole, fenticonazole, isoconazole, ketoconazole, luliconazole, miconazole, omoconazole, oxiconazole, sertaconazole, sulconazole, tioconazole, and triazoles. In some embodiments, the triazol comprises albaconazole, efinaconazole, epoxiconazole, fluconazole, isavuconazole, itraconazole, posaconazole, propiconazole, ravuconazole, terconazole, and voriconazole. In some embodiments, the allylamine comprises amorolfin, butenafine, naftifine, and terbinafine. In some embodiments, the echinocandins comprise anidulafungin, caspofungin, and micafungin.

In some embodiments, the bone graft composition exhibits antimicrobial efficacy or antifungal efficacy.

IX. Diluent Solution

A diluent solution is an aqueous media composed of water and other excipients that is able to make soluble the powder or dry slurry component of a bone graft composite material.

In some embodiments, the bone graft composition comprises a diluent or a solution that is added to the other components of the bone graft material in order to produce a malleable, moldable putty.

In some embodiments, the diluent is saline or water.

In a preferred embodiment, the diluent is a 0.9% saline solution as is commonly used in several medical and scientific applications.

In another preferred embodiment, the diluent is a 0.9% saline solution that contains acidifying agents.

In yet another preferred embodiment, the diluent is a 0.9% saline solution that contains acetic acid.

In still yet another preferred embodiment, the diluent is a 0.9% saline solution that contains acetic acid and any of the acidifying agents that contain a citric acid molecule, such as citric acid monohydrate or magnesium citrate, potassium citrate, or sodium citrate dihydrate.

In another preferred embodiment, the diluent is a 0.9% saline solution that contains acidifying agents and a liquid preparation of collagen.

X. Preparation of Bone graft Compositions

As used herein, the term "blending" refers to the physical process that combines or puts together non-aqueous materials to form one substance or mass that is a powder, or a dry slurry referred to herein as a "powder-dry slurry". Part of preparing a bone graft composite material requires the blending of the following constituents into a single powder-dry slurry composite material: calcium phosphates with hardening agents, iron excipients, agents that control the rate of curing, acidifying agents, and powdered collagen.

As used herein, the term "mixing" refers to a physical process that combines a powder-dry slurry with a diluent solution to form a paste, putty, or otherwise amorphous solid.

In some embodiments, between 0.1-mL to 15-mL of diluent will be added to 0.1-gram to 20-grams of the powder-dry slurry. In some embodiments, 0.5-mL of diluent will be added to 0.5-grams of powder-dry slurry. In some embodiments, 0.765-mL of diluent will be added to 1-gram of the powder-dry slurry. In some embodiments, 1-mL of diluent will be added to 1-grams of powder-dry slurry. In some embodiments, 1.5-mL of diluent will be added to 1.5-grams of powder-dry slurry. In some embodiments, 2-mL of diluent will be added to 2-grams of powder-dry slurry. In some embodiments, 2.5-mL of diluent will be added to 2.5-grams of powder-dry slurry. In some embodiments, 3-mL of diluent will be added to 3-grams of powder-dry slurry. In some embodiments, 3.5-mL of diluent will be added to 3.5-grams of powder-dry slurry. In some embodiments, 4-mL of diluent will be added to 4-grams of powder-dry slurry. In some embodiments, 4.5-mL of diluent will be added to 4.5-grams of powder-dry slurry. In some embodiments, 5-mL of diluent will be added to 5-grams of powder-dry slurry. In some embodiments, 5.5-mL of diluent will be added to 5.5-grams of powder-dry slurry. In some embodiments, 6-mL of diluent will be added to 6-grams of powder-dry slurry. In some embodiments, 6.5-mL of diluent will be added to 6.5-grams of powder-dry slurry. In some embodiments, 7-mL of diluent will be added to 7-grams of powder-dry slurry. In some embodiments, 7.5-mL of diluent will be added to 7.5-grams of powder-dry slurry. In some embodiments, 8-mL of diluent will be added to 8-grams of powder-dry slurry. In some embodiments, 8.5-mL of diluent will be added to 8.5-grams of powder-dry slurry. In some embodiments, 9-mL of diluent will be added to 9-grams of powder-dry slurry. In some embodiments, 9.5-mL of diluent will be added to 9.5-grams of powder-dry slurry. In some embodiments, 10-mL of diluent will be added to 10-grams of powder-dry slurry. In some embodiments, 10.5-mL of diluent will be added to 10.5-grams of powder-dry slurry.

In some embodiments, the bone graft composition has a density of 1.6-g/mL, 1.65-g/mL, 1.7-g/mL, 1.75-g/mL, 1.76-g/mL, 1.77-g/mL, 1.78-g/mL, 1.79-g/mL, 1.8-g/mL, 1.85-g/mL, 1.9-g/mL, or between 1-g/mL through 6-g/mL after mixing. In some embodiments, the bone graft composition has a density of 2-6 g/mL after mixing. In some embodiments, the bone graft composition has a density of 2-5 g/mL after mixing. In some embodiments, the bone graft composition has a density of 3.33-4.2 g/mL after mixing.

In some embodiments, the force required to extrude the bone graft composition through a cannula, tube, or syringe is less than 100-N/m. In some embodiments, the force required to extrude the bone graft composition through a cannula, tube, or syringe is less than 90-N/m. In some embodiments, the force required to extrude the bone graft composition through a cannula, tube, or syringe is less than 80-N/m. In some embodiments, the force required to extrude the bone graft composition through a cannula, tube, or syringe is less than 70-N/m. In some embodiments, the force required to extrude the bone graft composition through a cannula, tube, or syringe is less than 60-N/m.

XI. Delivery of Active Agents

A. Small Molecule Active Agents

It is a discovery of the present inventors that a bone graft material can be designed to more efficiently solubilize, sequester, and deliver a small molecule active agent.

In some embodiments, the bone graft composition comprises a small molecule active agent. A small molecule active agent is a chemical species that effects some cellular function and is contained or sequestered in the bone graft composite material.

The small molecule active agent is a chemical species derived from a protein, a synthetically derived chemical, or a chemical derived from plant or animal sources. The chemical species can be chemically altered prior to incorporation into the bone graft composite material or the chemical species can be in its native state prior to incorporation into the bone graft composite material.

The chemical properties, such as pH and osmolarity, of a diluent solution component of a bone graft can be designed so that the solubility of a small molecule active agent in the diluent solution is increased prior to mixing with the powdered or dry slurry components of a bone graft composition.

The chemical properties of the powder-dry slurry component of a bone graft can be designed so that when the powder-dry slurry component is mixed with a diluent, the small molecule active agent becomes less soluble and becomes sequestered in the material. Further, this property can be used to control elution and bioavailability of a small molecule active agent.

In some embodiments, the small molecule active agent can be a component of the diluent solution.

In some embodiments, the small molecule active agent can be a component of the powder-dry slurry components.

In some embodiments, the small molecule active agent can be a separate preparation, either in liquid form or as a lyophilized solid, that is added to the diluent.

In some embodiments, the small molecule active agent can be a separate preparation, either in liquid or as a lyophilized solid, that is added to the powder-dry slurry component.

In some embodiments, the small molecule is an opioid growth factor antagonist.

B. Additional Biologically Derived Active Agents

It is a discovery of the present inventors that a bone graft material can be designed to more efficiently solubilize, sequester, and deliver a biologically derived active agent.

In some embodiments, the bone graft composition comprises a biologically derived active agent. A biologically derived active agent is a biologically species that effects some cellular function and is contained or sequestered in the bone graft composite material.

The biologically derived active agent is a chemical species derived from a protein, a synthetically derived chemical, or derived from plant or animal sources. The biologically derived species can be chemically altered prior to incorporation into the bone graft composite material or the biologically derived species can be in its native state prior to incorporation into the bone graft composite material.

The chemical properties, such as pH and osmolarity, of a diluent solution component of a bone graft can be designed so that the solubility of a biologically derived active agent in the diluent solution is increased prior to mixing with the powdered or dry slurry components of a bone graft composition.

The chemical properties of the powder-dry slurry component of a bone graft can be designed so that when the powder-dry slurry component is mixed with a diluent, the biologically derived active agent becomes less soluble and becomes sequestered in the material. Further, this property can be used to control elution and bioavailability of a biologically derived active agent.

In some embodiments, the biologically derived active agent can be a component of the diluent solution.

In some embodiments, the biologically derived active agent can be a component of the powder-dry slurry components.

In some embodiments, the biologically derived active agent can be a separate preparation, either in liquid form or as a lyophilized solid, that is added to the diluent.

In some embodiments, the biologically derived active agent can be a separate preparation, either in liquid or as a lyophilized solid, that is added to the powder-dry slurry component.

Additional biologically derived active agent could be a bone morphogenetic protein (i.e. BMP2, BMP4, BMP7), a platelet derived growth factor (PDGF) protein (i.e. PDGF-alpha or PDGF-beta), a transforming growth factor (TGF) beta protein, a vascular endothelial growth factor (VEGF) protein, cyclopamine, purmorphamine, resveratrol, netrin proteins (i.e. netrin-1 or netrin-4), slit proteins (i.e. slit-1, slit-2, slit-3), repulsive guidance molecules (RGM) proteins, or WNT-proteins (i.e. WNT1, WNT5, WNT10, WNT11)

C. Opioid Growth Factor Receptor (OGFR) Antagonists

By "OGFR antagonist" is meant any small molecule active agent that inhibits, suppresses or causes the cessation of at least one OGFR-mediated biological activity.

In some embodiments, an OGFR antagonist is an OGFR binding antagonist, namely, a molecule that, interferes with, blocks or otherwise prevents the interaction or binding of the met5-ligand (OGF) to the OGFR.

An OGFR binding antagonist can function in two ways: First, the OGFR antagonist can compete with the met5-ligand for binding to the OGFR on the surface of the nuclear membrane, thereby interfering with, blocking or otherwise preventing the binding of the met5-ligand to the OGFR, without triggering the downstream signaling that would otherwise be induced by the binding of the met5-ligand to the OGFR. Alternatively, an OGFR binding antagonist can bind to or sequester PENK or the met5-ligand with sufficient affinity and specificity to substantially interfere with, block or otherwise prevent binding of met5-ligand to the OGFR, thereby inhibiting, suppressing or causing the cessation of at least one OGFR-mediated biological activity. Generally speaking, OGFR binding antagonists can be large molecules (e.g., antibodies) or small molecules (e.g., compounds of a molecular weight of less than 15-kD, 12-kD, 10-kD or even 8-kD), and can be a polypeptide, nucleic acid, or a synthetic small molecule compound. OGFR binding antagonists can be identified with any in vitro assay readily selected by one of skill in the art. For example, OGFR antagonists can be identified using the methods described in U.S. Pat. Nos. 5,882,944, 6,007,986, or U.S. Pat. No. 6,270,979.

In one embodiment, the OGFR binding antagonist is naloxone or a functional derivative thereof, naltrexone or a functional derivative thereof, or a combination thereof.

As used herein, a "functional derivative" refers to a derivative or analog that is structurally and functionally analogous to the originating molecule (e.g., maintains the function of naltrexone or naloxone as an OGFR antagonist). Naloxone and naltrexone analogs can be synthesized using standard synthetic procedures such as those described in March J., Advanced Organic Chemistry, 3rd Ed. (1985). Examples of naltrexone and naloxone functional derivatives include salt forms, e.g., naloxone hydrochloride dihydrate or naltrexone hydrochloride. Additional examples of naltrexone and naloxone functional derivatives suitable for use in the present methods include naltrexone and naloxone analogs disclosed in U.S. Patent Application Publication No. 2007/0197573 A1, U.S. Pat. No. 6,713,488, for example.

In another embodiment, an OGFR binding antagonist is derived from oxymorphone and binds to the OGFR, which includes naloxone, naltrexone, nalorphine, naloxonazine, levallorphan, nalmefene, cyprodime, cyclorphan, cyclazocine, oxilorphan, LY113878, MR2266, diprenorphine, WIN 44,441-3, naltindole, or norbinaltorphimine.

In still another embodiment, an OGFR binding antagonist is derived from trans-3,4-dimethyl-4-phenylpiperidine and binds to the OGFR, which includes LY99335, LY25506, LY117413, or LY255582.

In another embodiment, an OGFR binding antagonist is derived from the met5-enkephalin or leu-enkephalin peptides, binds to the OGFR, and minimally includes the following amino acid sequences as a means of targeting the OGFR: Tyr-Gly-Gly-Phe-Met (SEQ ID NO: 1) for those derived from met5-enkephalin or Tyr-Gly-Gly-Phe-Leu (SEQ ID NO:2) for those derived from the leu-enkephalin.

In still another embodiment, an OGFR binding antagonist is derived from the peptide antagonist 101174864 (N,N-diallyl-Tyr-Aib-Aib-Phe-Leu-OH; Aib=aminoisobutyticacid) or somatostatin analog CTP(D-Phe-Cys-Tyr-D-Trp-Lys-Thr-Pen-Thr-NH$_2$, SEQ ID NO: 4).

In other embodiments, the OGFR antagonist, instead of being an OGFR binding antagonist, is a molecule that disrupts the nuclear localization sequence found within OGFR:

(SEQ ID NO: 5)
251QSALDYFMFAVRCRHQRRQLVHFAWEHFRPRCKFVWGPQDKL

RRFKPSSL.

In still other embodiments, the OGFR antagonist employed in the present methods is a small-hairpin (sh)-RNA or a small-interfering (si)-RNA directed against the OGFR gene and effective in disrupting OGFR gene expression.

The OGFR antagonists described herein can be administered individually or in combination. Suitable combinations include, for example, naloxone and naltrexone; naloxone and/or naltrexone, in combination with another OGFR binding antagonist or another OGFR antagonist.

D. Delivery Systems and Carriers for Local Administration

In one aspect of the present disclosure the bone graft composite material is produced by mixing an appropriate diluent containing an active agent with a powder-dry slurry that is then administered directly and locally to a site of bone injury or surgical intervention where bone graft materials are normally placed to stimulate bone formation.

It is a discovery of the present inventors that a specific formulation of the diluent component and the powder-dry slurry components can be achieved to optimize the elution, sequestration, and bio-availability of an OGFR antagonist that share chemical properties with either naloxone, naltrexone, combinations of naloxone and naltrexone, or salts thereof.

In some embodiments, the OGFR antagonist is incorporated into the bone graft composite material such that the concentration in the material is about 1 nanomolar (nM) per cubic centimeter (1-nM/cc) to about 100-mM per cubic centimeter (100-mM/cc). In some embodiments, the concentration is 1-mM/cc, 1.25-mM/cc, 1.5-mM/cc, 1.75-mM/cc, 2.0-mM/cc, 3.0-mM/cc, 4.0-mM/cc, 5.0-mM/cc, 6.0-mM/cc, 7.0-mM/cc, 8.0-mM/cc, 9.0-mM/cc, and/or 20.0-mM/cc, 30.0-mM/cc, 40.0-mM/cc, 50.0-mM/cc, 60.0-mM/cc, 70.0-mM/cc, 90.0-mM/cc, 100-mM/cc.

In some embodiments, the concentration of an OGFR antagonist in the bone graft material is such that the elution rate from the material is between 0.001-pM per second to 10-mM per day.

In some embodiments, the cumulative dose that arises from elution of an OGFR agonist during the period when the small molecule is released from the bone graft material through diffusion or other physical effects that are the result of the normal degradation of the bone graft material once implanted are 0.8-mM, 1-mM, 1.1-mM, 1.15-mM, 1.2-mM, 1.25-mM, 1.3-mM, 1.35-mM, 1.4-mM, 1.45-mM, 1.5-mM, 1.55-mM, 1.6-mM, 1.65-mM, 1.7-mM, 1.75-mM, 1.8-mM, 1.9-mM, 2-mM, 2.7-mM, 3-mM, 3.6-mM, 4-mM, 4.5-mM, 5-mM, 5.4-mM, 6-mM, 6.3-mM, 7-mM, 7.2-mM, 8-mM, 8.1-mM, 9-mM, or 10-mM.

In a preferred embodiment, the OGFR antagonist is naloxone hydrochloride with a concentration of 0.2-mg/cc (0.5-mM/cc), 0.25-mg/cc (0.625-mM/cc), 0.3-mg/cc (0.75-mM/cc), 0.35-mg/cc (0.875-mM/cc), 0.4-mg/cc (1-mM/cc), 0.45-mg/cc (1.125-mM/cc), 0.5-mg/cc (1.25-mM/cc), 0.55-mg/cc (1.375-mM/cc), 0.6-mg/cc (1.5-mM/cc), 0.65-mg/cc (1.625-mM/cc), 0.7-mg/cc (1.75-mM/cc), 0.75-mg/cc (1.875-mM/cc), 0.8-mg/cc (2-mM/cc), 0.85-mg/cc (2.125-mM/cc), 0.9-mg/cc (2.25-mM/cc), 0.95-mg/cc (2.375-mM/cc), or 1-mg/cc (2.5-mM/cc).

E. Compositions and Administration

The methods and compositions herein may be provided in the form of a kit. A "kit" is herein defined as a package and containing several individual parts that show a complementary effect when applied together. In this aspect, the effect achieved by a kit and the pharmaceutical composition are similar. The kit may optionally include instructions for using the pharmaceutical compositions.

The present invention is further illustrated by, though in no way limited to, the following examples.

EXAMPLE

Working Example 1: Bone Graft Materials

In the first specific example, the preferred embodiment of the dry slurry component of the bone graft material contains the following as a percentage of weight: 1) between 1% and 7% of iron (III) chloride, 2) between 8.5% and 11% calcium phosphate dibasic, 3) between 9.5% and 12.5% calcium phosphate tribasic, 4) between 15% and 17% hydroxyapatite, 5) between 3% and 6% beta-tricalcium phosphate, 6) between 5% and 7.5% sodium phosphate dibasic, 7) between 12% and 16% sodium carbonate, 8) between 2% and 6% calcium oxide, 9) between 4% and 6% magnesium oxide, 10) between 0.5% and 2.5% L-ascorbic acid, and 11) between 19% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after 3-minutes, turns a light brown color upon setting, and achieves a peak temperature of 29.7-degrees Celsius after 2-minutes of mixing.

In the second specific example, the preferred embodiment of the dry slurry component of the bone graft material contains the following as a percentage of weight: 1) between 5% and 10% of iron (III) citrate, 2) between 8% and 11% calcium phosphate dibasic, 3) between 9% and 12.5% calcium phosphate tribasic, 4) between 13% and 17% hydroxyapatite, 5) between 3% and 6% beta-tricalcium phosphate, 6) between 4% and 7.5% sodium phosphate dibasic, 7) between 11% and 15% sodium carbonate, 8) between 2% and 6% calcium oxide, 9) between 4% and 6% magnesium oxide, 10) between 0.5% and 2.5% L-ascorbic acid, and 11) between 19% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after 5-minutes, turns a dark chocolate brown color upon setting, and achieves a peak temperature of 28.6-degrees Celsius after 30-seconds of mixing.

In the third specific example, the preferred embodiment of the dry slurry component of the bone graft material contains the following as a percentage of weight: 1) between 1% and 5% of iron (III) oxide, 2) between 8% and 11% calcium phosphate dibasic, 3) between 9% and 13% calcium phosphate tribasic, 4) between 14% and 18% hydroxyapatite, 5) between 3% and 6.5% beta-tricalcium phosphate, 6) between 4% and 8% sodium phosphate dibasic, 7) between 12% and 16% sodium carbonate, 8) between 2% and 6% calcium oxide, 9) between 4% and 6% magnesium oxide, 10) between 0.5% and 2.5% L-ascorbic acid, and 11) between 20% and 24% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after 3.5-minutes, turns white with iron gray inclusions upon setting, and achieves a peak temperature of 29.8-degrees Celsius after 30-seconds of mixing.

In the fourth specific example, the preferred embodiment of the dry slurry component of the bone graft material contains the following as a percentage of weight: 1) between 5% and 10% of iron (III) phosphate, 2) between 8% and 11% calcium phosphate dibasic, 3) between 9% and 12.5% calcium phosphate tribasic, 4) between 13% and 17% hydroxyapatite, 5) between 3% and 6% beta-tricalcium phosphate, 6) between 4% and 7.5% sodium phosphate dibasic, 7) between 12% and 16% sodium carbonate, 8) between 2% and 6% calcium oxide, 9) between 4% and 6% magnesium oxide, 10) between 0.5% and 2.5% L-ascorbic acid, and 11) between 19% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after 3.5-minutes, turns a light tan color upon setting, and achieves a peak temperature of 33.5-degrees Celsius after 1.5-minutes of mixing.

In the fifth specific example, the preferred embodiment of the dry slurry component of the bone graft material contains the following as a percentage of weight: 1) between 5% and 10% of ammonium iron (III) citrate, 2) between 8% and 11% calcium phosphate dibasic, 3) between 9% and 12.5% calcium phosphate tribasic, 4) between 13% and 17% hydroxyapatite, 5) between 3% and 6% beta-tricalcium phosphate, 6) between 4% and 7.5% sodium phosphate dibasic, 7) between 11% and 15% sodium carbonate, 8) between 2% and 6% calcium oxide, 9) between 4% and 6% magnesium oxide, 10) between 0.5% and 2.5% L-ascorbic acid, and 11) between 19% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after 3-minutes, turns a brown color upon setting, and achieves a peak temperature of 30.3-degrees Celsius after 1.5-minutes of mixing.

In the sixth specific example, the preferred embodiment of the dry slurry component of the bone graft material contains the following as a percentage of weight: 1) between 5% and 12% of iron (III) sulfate, 2) between 8% and 11% calcium phosphate dibasic, 3) between 9% and 12.5% calcium phosphate tribasic, 4) between 13% and 17% hydroxyapatite, 5) between 3% and 6% beta-tricalcium phosphate, 6) between 4% and 7.5% sodium phosphate dibasic, 7) between 11% and 15% sodium carbonate, 8) between 2% and 6% calcium oxide, 9) between 4% and 6% magnesium oxide, 10) between 0.5% and 2.5% L-ascorbic acid, and 11) between 18% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, and 3) between 0.1% and 2% citric acid monohydrate. In this embodiment, no active agent will be incorporated. Upon mixing the dry slurry component and the diluent, the bone graft material becomes moldable after approximately 2.5-minutes, turns a dark brown-color upon setting, and achieves a peak temperature of 38-degrees Celsius after 1.5-minutes of mixing.

In the seventh specific example, the preferred embodiment of the dry slurry component of the bone graft material contains the following as a percentage of weight: 1) between 5% and 12% of iron (III) sulfate, 2) between 8% and 11% calcium phosphate dibasic, 3) between 9% and 12.5% calcium phosphate tribasic, 4) between 13% and 17% hydroxyapatite, 5) between 3% and 6% beta-tricalcium phosphate, 6) between 4% and 7.5% sodium phosphate dibasic, 7) between 11% and 15% sodium carbonate, 8) between 2% and 6% calcium oxide, 9) between 4% and 6% magnesium oxide, 10) between 0.5% and 2.5% L-ascorbic acid, and 11) between 18% and 23% powdered type-I collagen. The preferred embodiment of the diluent component will be a solution between 0.5-mL and 12.5-mL in volume composed of the following: 1) a 0.9% saline solution, 2) between 2% and 6% of acetic acid, 3) between 0.1% and 2% citric acid monohydrate, and 4) between 0.01% and 2% of naloxone hydrochloride. Upon mixing the dry slurry component and the diluent, the bone graft material becomes moldable after approximately 2.5-minutes, turns a dark brown-color upon setting, and achieves a peak temperature of 38-degrees Celsius after 1.5-minutes of mixing.

Further, in the seventh preferred embodiment that contains iron (III) sulfate, the bone graft material was mixed as described and placed into cultures to assess osteoblast differentiation in conformance with ASTM F3106-14. The mouse osteoblast (bone cell) progenitor cell line, the MC3T3-E1 (MC3) cells, were seeded in cultures as micro-masses ($2.5 \times 10^5$ cells per micro-mass suspended in 20-microL of a Matrigel+DMEM solution) and allowed to grow for 120-hours and maintained in growth media (DMEM with 20% fetal calf serum). Control cultures (Control) were maintained in growth media. Induction control cultures (Induced) were stimulated to become bone cells with media supplemented with ascorbic acid, beta-glycerophosphate, and dexamethasone. In this example, the MC3 micro-mass spheroids were allowed to grow for an additional 7-days, after which experimental groups were stained with alizarin red and analyzed for mineral quantity using a One-way ANOVA with Bonferonni's Correction to assess differences.

Results demonstrate that cultures containing the iron sulfate material (with or without an active agent) increased bone formation significantly based on alizarin red staining (FIG. 1A) relative to Induction and Control cultures. The size of the micro-mass spheroid and the mineral contained in each micro-mass spheroid was quantified to identify the Mineral Area Fraction. The mineral area fraction for the micro-mass spheroids that had the iron (III) sulfate bone graft material had significantly more mineral than control cultures 4-fold (*=$p<0.0046$) (FIG. 1B). From these data we can conclude that the iron (III) sulfate bone graft material is osteoconductive and osteopromotive. An inter-group analysis demonstrated that the bone formation in the bone graft without naloxone demonstrated that the bone graft material component of increased mineral formation 4-fold (*=p<0.0046) in culture versus controls and the wells chemically induced to make bone. The addition of 0.4-mg of naloxone to the bone graft material increased mineral formation an additional 25% (x=p<0.0001) versus the Control Bone graft implant group that did not contain naloxone.

Working Example 2: Use of Bone Graft Implant in Spine Fusion Procedures

Working example 2 shows a lateral lumbar interbody fusion (LLIF) procedure using the claimed bone grafts. In particular, this study is performing LIF with a bone graft containing an osteoconductive, synthetic bone graft material that includes the small molecule naloxone hydrochloride. The synthetic bone graft is composed of type I bovine collagen, hydroxyapatite (HA), β-tricalcium phosphate, and other calcium salts and some excipients. The synthetic bone graft composition containing naloxone hydrochloride is hereinafter referred to as Composition ZF.

The present disclosure provides a method of repairing a bone defect in a patient in need thereof, comprising applying the bone graft composition such as Composition ZF, wherein the method comprises a surgical intervention such as lumbar interbody fusion (LIF). In some embodiments, the LIF procedure comprises anterior LIF (ALIF), lateral LIF (LLIF), transforaminal LIF (TLIF), and posterior LIF (PLIF). In some embodiments, the LIF procedure relieves associated pathologies, such as degenerative disc disease of a subject determined through radiography, by the creation of a bone defect via a surgical intervention. In some embodiments, the LIF procedure relieves associated neuromuscular deficits or physical deficits of a subject as determined by the Oswestry Disability Index (ODI) of the subject, by neurological evaluation of the subject, or by radiography of the subject.

Background on LIF Procedures

LIF procedures are distinguished based on their anatomical approach and implanted hardware, and include anterior LIF (ALIF), lateral LIF (LLIF), transforaminal LIF (TLIF), and posterior LIF (PLIF). LIF procedures encompass the removal of disc material that is believed to be involved in the source of back or leg pain and the replacement of an interbody cage or spacer to facilitate arthrodesis of the involved disc and vertebrae. The number of LIF procedures has increased significantly over the past 20 years due to evolutions in surgical techniques, implants, imaging modalities, and demand.

As a result of the potential challenges with local autograft, allograft and orthobiologics are regularly used in conjunction with, or as a substitute for, local bone to meet the needs of bone grafting in LIF procedures. Although there has been significant advancement in the development of bone graft materials, there remains a need for a bone graft material that produces biomechanically strong solid fusions and has a favorable safety profile.

Tests of the Bone Graft Composition

Indications for the Composition ZF bone graft includes spinal fusion procedures in skeletally mature patients with degenerative disc disease (DDD) at one level from L2-L5. DDD is defined as discogenic back pain with degeneration of the disc and/or Grade II spondylolisthesis at the involved level as confirmed by patient history and radiographic assessment. Patients that receive Composition ZF bone graft have at least three months of failed non-operative treatment prior to treatment with the Composition ZF bone graft device. The lateral lumbar interbody fusion (LLIF) procedure uses a commercially available polyetheretherketone (PEEK), porous PEEK, or hydroxyapatite (HA) PEEK spacer with a supplemental fixation system (a lateral plate or bi-lateral pedicle screws) to implant the Composition ZF bone graft.

Trial Design

Subjects undergo LLIF with supplemental fixation consisting of supplemental fixation system or a lateral plate. In an Experimental Arm, the Composition ZF bone graft packs the hollow area in the interbody spacer. In a Control Arm, allogenic bone graft (i.e., DBX Putty, Demineralized Bone Matrix)+/−bone marrow aspirate packs the hollow area in the interbody spacer.

Surgical eligibility criteria include the following: 1) Patients between 22 and 75 years of age. 2) Diagnosis of degenerative disc disease (DDD) that is accompanied by back pain with or without leg pain at a single level of the spine between the second lumbar vertebral bone (L2) and the fifth lumbar vertebral bone (L5) confirmed via the collection of a patient history and a radiographic assessment (e.g., plain X-radiographs, computed tomography (CT), or magnetic resonance imaging (MRI)). 3) Spinal instability identified via X-radiographs taken to during flexion/extension movement that show angulation≥5 degrees and/or translation≥4 mm of the affected vertebral bones. 4) Pathological findings from imaging studies that show osteophyte formation, decreased disc height, ligamentous thickening, disc degeneration/herniation, facet joint degeneration, dark disc appearance on MRI, foraminal narrowing, or loss of foraminal height. 5) DDD is defined as discogenic back pain with degeneration of the disc confirmed by patient history and radiographic assessment. DDD patients may also have up to Grade I spondylolisthesis at the involved spinal level. 6) Patients should have had at least six months of failed non-operative treatment prior to surgical intervention. 7) Lateral lumbar interbody fusion (LIF) procedures will use a PEEK or titanium spacer with a supplemental fixation system (a lateral plate or bi-lateral pedicle screws).

Working Example 3: Use of Bone Void Filler for Bony Voids or Gaps that are not Intrinsic to the Stability of the Bony Structure The use of the bone graft compositions disclosed herein includes using the bone graft compositions as bone void filler for bony voids or gaps that are not intrinsic to the stability of the bony structure. In particular, Composition ZB bone graft (a composition identical to Composition ZF except that it lacks naloxone) is gently packed into bony voids or gaps of the skeletal system (e.g., the posterolateral spine, pelvis, ilium, and/or extremities).

Accordingly, the present disclosure provides a method of repairing a bone defect in a patient in need thereof, comprising applying the bone graft compositions disclosed herein to the bone defect, wherein the bone defect comprises a void or gap of the bony skeletal system, wherein the void or gap is not intrinsic to the stability of the bony skeletal structure, and wherein the bone graft compositions is packed into the void or gap. In some embodiments, these defects are surgically created osseous defects or osseous defects created from traumatic injury to the bone. Composition ZB bone graft resorbs and is replaced with bone during the healing of these defects Working Example 4: Safety and the Effectiveness of Composition ZF Bone Graft in Subjects Undergoing a Reconstructive Procedure to Stabilize the Humerus after Resection of a Metastatic Breast Cancer Tumor This study evaluates safety and effectiveness of the Composition ZF Bone graft in reconstruction of the Metaphysis-Diaphysis of the humerus by using an Intercalary Allograft and Plate Fixation following malignant tumor resection such as a malignant breast cancer metastatic tumor.

Study Design

Subject of the experimental arm receives the Composition ZF Bone graft that contains an osteoconductive, synthetic bone graft material and the small molecule naloxone hydrochloride. The synthetic bone graft is composed of type I bovine collagen, hydroxyapatite (HA), β-tricalcium phosphate, and other calcium salts and some excipients. Subjects of the control arm receive the allograft fixed with plates and screws, and the allograft is filled with polymethylmethacrylate (PMMA) bone cement. Establishing non-inferiority of the Experimental Arm compared to the Control Arm confirms the effectiveness of the trial.

Working Example 5: Safety and the Effectiveness of Composition ZF Bone Graft in Subjects Undergoing a Reconstructive Procedure to Stabilize the Femur, Tibia, or Pelvis after Resection of a Metastatic Breast Cancer Tumor This study evaluates safety and effectiveness of the Composition ZF Bone graft in reconstruction of the proximal femur, distal femur, tibia or pelvis, by using an intramedullary nail, intramedullary locking nail, or cephalomedullary nail, plate fixation, or some combination orthopedic fixation devices following malignant tumor resection such as a malignant breast cancer metastatic tumor. Following removal of the tumor, polymethylmethacrylate (PMMA) bone cement will be placed into the defect to provide mechanical stability, and Composition ZF will be places around the implant/PMMA bone cement construct adjacent to bone tissue.

Study Design

Subject of the experimental arm will receive after tumor removal an appropriate fixation device with PMMA bone cement and the Composition ZF Bone graft that contains an osteoconductive, synthetic bone graft material and the small molecule naloxone hydrochloride. The synthetic bone graft is composed of type I bovine collagen, hydroxyapatite (HA), β-tricalcium phosphate, and other calcium salts and some excipients. Subjects of the control arm will receive after tumor removal an appropriate fixation device and PMMA bone cement. Establishing non-inferiority of the Experimental Arm compared to the Control Arm confirms the effectiveness of the trial.

What is claimed is:

1. A method of treating a patient having a cancer selected from the group consisting of lung cancer, breast cancer and prostate cancer, comprising identifying a bone defect in the patient caused by the cancer or resulting from treatment of the cancer, locally administering at the site of the bone defect in the cancer patient in need thereof a composition consisting of a calcium phosphate, an OGFR antagonist, an iron excipient, an optional curing agent, and at least one of the following: an acidifying agent, collagen, and a diluent saline solution, wherein the composition provides a therapeutically effective amount of the iron excipient that increases mineral formation at the site of the bone defect, and wherein the iron excipient is iron (III) sulphate.

2. The method of claim 1, wherein the calcium phosphate comprises biphasic calcium phosphate particles.

3. The method of claim 2, wherein the biphasic calcium phosphate particles comprise hydroxyapatite and tricalcium phosphate.

4. The method of claim 3, wherein the biphasic calcium phosphate particles comprise about 20-60% hydroxyapatite and about 40-80% tricalcium phosphate.

5. The method of claim 1, wherein the OGFR antagonist is delivered at a controlled rate.

6. The method of claim 5, wherein the OGFR antagonist is selected from the group consisting of naloxone, naltrexone, and a salt thereof.

7. The method of claim 1, wherein the composition comprises the acidifying agent and the acidifying agent is at least one of ascorbic acid, magnesium citrate, potassium citrate, sodium citrate, citric acid monohydrate, and acetic acid.

8. The method of claim 1, wherein the curing agent is in the composition and the curing agent is selected from the group consisting of calcium oxide, magnesium oxide, sodium phosphate dibasic, sodium pyrophosphate tetrabasic, sodium orthophosphate, and sodium phosphate monobasic.

9. The method of claim 1, wherein the cancer is lung cancer.

10. The method of claim 1, wherein the cancer is prostate cancer.

11. The method of claim 1, wherein the cancer is breast cancer.

12. The method of claim 11, wherein the bone defect is caused by resection of a metastatic breast cancer tumor in the patient.

13. The method of claim 1, wherein the OGFR antagonist is naloxone.

\* \* \* \* \*